United States Patent [19]

Pelosi, Jr.

[11] 4,012,416
[45] Mar. 15, 1977

[54] 2-[5-(3-TRIFLUOROMETHYLPHENYL)2-FURYL]IMIDAZOLE HYDROCHLORIDE

[75] Inventor: Stanford S. Pelosi, Jr., Norwich, N.Y.

[73] Assignee: Morton-Norwich Products, Inc., Norwich, N.Y.

[22] Filed: Jan. 29, 1976

[21] Appl. No.: 653,442

[52] U.S. Cl. .............................. 260/309; 424/273; 260/347.7

[51] Int. Cl.$^2$ ....................................... C07D 405/04

[58] Field of Search .................................... 260/309

[56] References Cited

UNITED STATES PATENTS 2,710,870  6/1955  Lawson ............................ 260/309
3,600,399  8/1971  Berkelhammer et al. ......... 260/309

FOREIGN PATENTS OR APPLICATIONS 1,215,858  12/1970  United Kingdom ............... 260/309

OTHER PUBLICATIONS

Schubert et al., Chem. Abst. 1963, vol. 58, columns 2445–2446.

*Primary Examiner*—Natalie Trousof
*Attorney, Agent, or Firm*—Anthony J. Franze

[57] ABSTRACT

2-[5-(3-Trifluoromethylphenyl)-2-furyl]imidazole hydrochloride is an effective skeletal muscle relaxant.

1 Claim, No Drawings

2-[5-(3-TRIFLUOROMETHYLPHENYL)2-FURYL]IMIDAZOLE HYDROCHLORIDE

This invention relates to the compound 2-[5-(3-trifluoromethylphenyl)-2-furyl]imidazole hydrochloride of the formula:

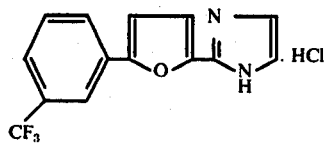

This compound possesses pharmacologic activity. In particular it exhibits skeletal muscle relaxant activity when administered perorally or intravenously to warm-blooded animals. Thus when administered intravenously in a pharmaceutically acceptable solvent, such as tetrahydrofurfuryl alcohol, at a dose of about 25 mg/kg to rats, inhibition of the twitch response of the gastrocnemius muscle is elicited.

This compound is preferably prepared in accordance with the following example:

To a stirring mixture of 110 g (0.36 mole) of ethyl 5-(3-trifluoromethylphenyl)-2-furimidate hydrochloride and 1700 ml of absolute ethanol was added 38 g (0.36 mole) of aminoacetaldehyde dimethyl acetal with dissolution. The reaction solution was refluxed for 6 hours, the solvent was removed on the Calab evaporator, and the residual solid was washed in hexane and air dried to yield 106 g (78%) of N'-(2,2-dimethoxyethyl)-5-(3-trifluoromethylphenyl)-2-furamidine hydrochloride. A sample was recrystallized from acetonitrile and dried at room temperature to give a m.p. of 173°–174°.

A mixture of 50 g (0.13 mole) of the above compound and 500 ml of 3N HCl was heated overnight at 55°–70°. After cooling, the solid was collected by filtration, recrystallized from isopropanol, and air dried to yield 26 g (63%) of 2-[5-(3-trifluoromethylphenyl)-2-furyl]imidazole hydrochloride. An analytical sample was prepared by recrystallizing a sample twice from isopropanol, m.p. ca. 235°.

Anal. Calc'd. for $C_{14}H_9F_3N_2O\cdot HCl$: C, 53.51; H, 3.21; N, 8.92. Found: C, 53.35; H, 3.32; N, 8.69.

What is claimed is:

1. The compound 2-[5-(3-trifluoromethylphenyl)-2-furyl]imidazole hydrochloride.